United States Patent [19]

Ching

[11] 4,349,607
[45] Sep. 14, 1982

[54] UV STABILIZERS, COATING COMPOSITIONS AND COMPOSITE STRUCTURES OBTAINED THEREFROM

[75] Inventor: Ta-Yen Ching, Schenectady, N.Y.

[73] Assignee: General Electric Company, Schenectady, N.Y.

[21] Appl. No.: 248,182

[22] Filed: Mar. 30, 1981

Related U.S. Application Data

[62] Division of Ser. No. 100,441, Sep. 5, 1979, Pat. No. 4,288,631.

[51] Int. Cl.³ .............................................. C08K 5/13
[52] U.S. Cl. .................................... 428/412; 524/114; 524/359; 428/502; 428/522
[58] Field of Search .................. 428/412, 502, 522; 568/333; 260/45.95 F; 524/359

[56] References Cited

U.S. PATENT DOCUMENTS

| | | | |
|---|---|---|---|
| 2,659,709 | 11/1953 | Daglisch et al. | 260/45.95 F |
| 2,976,259 | 3/1961 | Hardy et al. | 260/45.95 F |
| 3,403,183 | 9/1968 | Dobratz et al. | 260/45.95 F |
| 3,879,470 | 4/1975 | Munakata et al. | 260/45.95 F |
| 4,126,660 | 11/1978 | Lempkowicz et al. | 260/45.95 F |
| 4,208,465 | 6/1980 | Chang | 260/45.95 F |

OTHER PUBLICATIONS

Van Allen et al., J. Organic Chemistry, 19, (1954), pp. 1243–1251.
Jones et al., J. Chemical Society of London, 1932, Part I, pp. 1689–1693.

*Primary Examiner*—V. P. Hoke
*Attorney, Agent, or Firm*—William A. Teoli; James C. Davis, Jr.

[57] ABSTRACT

Certain 3-alkylhydroxybenzophenone derivatives, such as 2,4-dihydroxy-3-methylbenzophenone have been found to be superior as UV stabilizers for a variety of organic polymeric substrates. Coating compositions of such stabilizers in organic resins, for example, melamine can be used to protect such polymeric substrates from the effects of exposure to UV radiation.

5 Claims, No Drawings

UV STABILIZERS, COATING COMPOSITIONS AND COMPOSITE STRUCTURES OBTAINED THEREFROM

This application is a division of application Ser. No. 100,441, filed Sept. 5, 1979, now U.S. Pat. No. 4,288,631.

CROSS REFERENCE TO RELATED APPLICATIONS

Reference is made to the copending application of James E. Moore, for Melamine Coatings, Ser. No. 935,590, filed Aug. 21, 1978, now U.S. Pat. No. 4,197,392. In addition, reference is also made to my copending application Ser. No. 100,442, filed Dec. 5, 1979, now abandoned, for UV Stabilizers, Coating Compositions and Composite Structures Obtained Therefrom, filed concurrently herewith and assigned to the same assignee as the present invention.

BACKGROUND OF THE INVENTION

Prior to the present invention, 2,4-dihydroxybenzophenones such as Eastman 2,4-DHPB, manufactured by the Eastman Kodak Company, Rochester, N.Y., were used extensively as ultraviolet screens for the protection of various thermoplastics, such as polycarbonates, polyesters, etc. In determining whether a particular UV stabilizer is effective, the stabilizer can be incorporated into an organic resin, for example, melamine at about a 3% by weight of the total coating composition and thereafter applied onto the surface of the thermoplastic substrate, for example, a sheet and cured. Those skilled in the art, however, are constantly evaluating various UV stabilizers in order to optimize the protection afforded by such stabilizers to the thermoplastic substrates which are treated with such materials.

STATEMENT OF THE INVENTION

The present invention is based on the discovery that UV stabilizers having the formula,

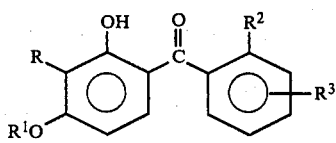

where R is a $C_{(1-8)}$ alkyl radical, $R^1$ is selected from the class consisting of hydrogen, and $C_{(3-8)}$ alkyl, $R^2$ is selected from the class consisting of hydrogen, hydroxy, methyl and OR, and $R^3$ is a member selected from the class consisting of hydrogen, hydroxy, R, OR, and $C_{(1-8)}$ hydroxy-alkoxy, and glycidyl alkoxy have been found to be superior UV stabilizers for a variety of thermoplastic substrates.

In addition to the above described UV stabilizers of formula (1), there is also provided by the present invention coating compositions comprising (A) an organic resin selected from the class consisting of melamine resin, acrylic resin, and silicone resin and (B) a stabilizing amount of the UV stabilizer of formula (1).

A third aspect of the present invention is directed to composite structures comprising (C) a thermoplastic substrate, (D) the cured coating of an organic resin selected from the class consisting of a melamine resin, acrylic resin and a silicone resin, and a stabilizing amount of a UV stabilizer of formula (1).

There are included by the UV stabilizers of formula (1), dihydroxybenzophenone compounds of the formula,

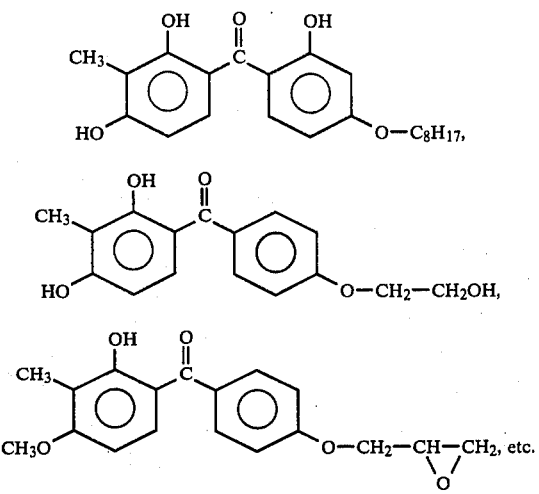

Included within the organic resins which can be employed in the practice of the present invention to make the above described coating compositions are various melamine resins such as melamine compounds of the formula,

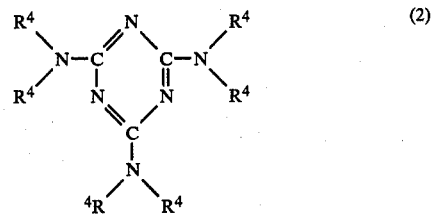

where the $R^4$ groups are selected from the class of H, $-CH_2OH$, and $-CH_2O(CH_2)_xH$, where x is an integer of from 1 to 4, which can be used with polyhydroxy aromatic or aliphatic monomers or polymers, polymethylmethacrylate having a molecular weight in the range of from 50,000 to 150,000, polyethylmethacrylate, etc.; silicone resins consisting essentially of chemically combined $(R^5)_nSiO\ (4-n)/(2)$ units, where $R^5$ is methyl or a methyl, phenyl mixture and n has an average value of 1 to 1.8.

Some of the polyhydroxy aromatic or aliphatic compounds which can be utilized in combination with the melamine compound of formula (2), for example, resorcinol, 2,2'-methylenediphenol, 2,4'-methylenediphenol, 2,4'-diisopropylidenediphenol, 4,4'-(cyclohexylidene)-diphenol, and 4,4'-dihydroxydiphenyl, and 4,4'-dihydroxydiphenylsulfone. Representative aliphatic compounds are alcohols which include ethylene glycol, diethylene glycol, triethylene glycol, tetraethylene glycol, propylene glycol, 1,3-propanediol, 1,4-butanediol, 1,5-pentanediol, 1,2,3-propanetriol, pentaerythritol and sorbitol. Additional polyhydroxy compounds are hydroxyl containing epoxy resin, a soluble cellulose derivative, a vinyl polymer having free hydroxyl groups, such as poly(vinyl alcohol) or partial saponified poly(vinyl acetate). The polyfunctional hydroxyl compound (e.g. polyol) can also contain carboxyl and amine groups but should contain at least two hydroxyl groups. Additional silicones which can be used in the practice of the invention are shown by Kirk-Othmer, Vol. 18, Second Edition, p. 221-260 of the Encyclopedia of Chemical Technology (1969) John Wiley and Sons, New York.

In preparing the coating compositions used in the practice of the present invention there generally can be employed from 0.5% to 10% of the UV stabilizer of formula (1) based on the weight of UV stabilizer and organic resin. In particular situations, the above shown melamine compound of formula (2) can be used in combination with the UV stabilizer in the absence of the polyhydroxy aromatic or aliphatic compound.

In preparing the coating composition, the UV stabilizer can be blended with the organic resin in the presence of a suitable solvent such as N-butanol, methanol and the like. In addition, a suitable acid catalyst can be employed such as benzene sulfonic acid or sulfamic acid along with a surface active agent to assist in forming a film of the composition. There can be utilized from about 0.1% to about 3%, by weight of the acid catalyst, while suitable surface active agents which are commercially available are, for example, BYK-300 of the Millinckrodt Chemical Company.

The coating composition can be applied onto a suitable organic thermoplastic substrate by conventional means such as spraying, dipping, etc. The thickness of the applied coating is not critical but effective results can be achieved at thicknesses of between about 0.05 mil and 1.0 mil. In instances where the applied coating is the melamine, cure can be accomplished at a temperature between about 100° to 150° C. at a period of from about 15 minutes to about 4 hours in an air oven.

Alternatively, the UV stabilizer can be incorporated into the organic thermoplastic polymer by adding it to or dry blending it with the powdered polymer prior to extrusion. As a result, the stabilizer is distributed throughout the extruded part and can be present at about 0.1% to 1% by weight.

Further, the UV stabilizers of the present invention can be incorporated onto the surface of the organic thermoplastic substrate by surface impregnation in accordance with German Pat. No. 1,171,888 by dipping the substrate into a solution of the stabilizers.

Included by the organic thermoplastic substrates which can be used in the practice of the present invention are, for example, polycarbonates, polyester carbonates, polyarylates, polycarbonate-polysiloxane copolymers, polystyrene, polyvinylchloride, ABS polymers, poly(2,6-dimethylphenylene oxide), etc.

In order that those skilled in the art will better able to practice the invention, the following examples are given by way of illustration and not by way of limitation. All parts are by weight.

EXAMPLE 1

A mixture of 18 parts of boron trifluoride, 25 parts of 2-methyl resorcinol, 25 parts of benzoic acid and 100 parts of tetrachloroethane was heated with stirring at 80° C. for 4 hours. The mixture was then poured into 300 parts of water containing 55 parts of sodium acetate. A solid cake was obtained upon filtering the mixture and extracting it with a 5% aqueous sodium hydroxide solution. After neutralization, the precipitate was collected and purified by recrystallization from methanol-water. There was obtained a 70% yield of product having a melting point of 173°-174° C. Based on NMR spectra, CH analysis and method of preparation the product was 2,4-dihydroxy-3-methylbenzophenone.

EXAMPLE 2

The procedure of Example 1 was repeated, except that p-methoxybenzoic acid was substituted for benzoic acid. There was obtained a 66% yield of product having a melting point of 194°-195° C. Based on method of preparation, CH analysis and NMR spectra, the product was 2,4-dihydroxy-4'-methoxy-3-methylbenzophenone.

EXAMPLE 3

The procedure of Example 1 was repeated except that p-hydroxybenzoic acid was used in place of benzoic acid. There was obtained a 79% yield of product having a melting point of 227°-228° C. Based on its method of preparation, CH analysis and its NMR spectra the product was 3-methyl-2,4,4'-trihydroxy benzophenone.

EXAMPLE 4

A study was made to determine the photostability of 2,4-dihydroxy-3-methylbenzophenone and 2,4-dihydroxybenzophenone. There were prepared methanol solutions of $6 \times 10^{-M}$ of the respective stabilizers which were then photolyzed with a 450 watt medium pressure mercury lamp while in 1 cm cuvettes in a carrousel photolysis apparatus. The 2,4-dihydroxybenzophenone solution visibly turned yellow after 3 minutes photolysis and its UV spectrum was completely altered after 10 minutes photolysis. In contrast, the 2,4-dihydroxy-3-methylbenzophenone solution did not change its color or its UV spectrum after over the 20 minute photolysis.

EXAMPLE 5

A coating blend of 750 parts of hexamethoxymethyl melamine and 750 parts of caprolactone polyol was mixed with 7.5 parts of a surface active agent, BYK-300 of the Mallinckrodt Chemical Company along with 1.5%, based on the weight of the mixture, of p-toluene sulfonic acid. Several hydroxybenzophenone stabilizers were then respectively blended with the coating blend to produce blends having 3% by weight of the stabilizer based on solids. The respective stabilized blends were then coated on polycarbonate film strips which were then cured at 125° C. for 1 hour. The coated Lexan ® resin was then placed under a bank of General Electric RS sunlamps and aged. In accordance with ASTM D-1925-70, the prime tristimulas values are measured by color master model V of the Manufacturers Engineering and Equipment Corporation and the yellowing index values, YI, calculated. The following table shows the results obtained after 1000 hours aging, where ΔYI indicate the increase of yellowing index values over this period.

TABLE I

| Stabilizer | ΔYI |
|---|---|
| 2-hydroxy-4-octoxybenzophenone | 12 |
| 2,4-dihydroxy-benzophenone | 6 |
| 2,4-dihydroxy-3-methylbenzophenone | 2.25 |
| 2,4-dihydroxy-4'-methoxy-3-methylbenzophenone | 2 |
| 3-methyl-2,4,4'- | |

TABLE I-continued

| Stabilizer | ΔYI |
| --- | --- |
| trihydroxybenzophenone | 1.5 |

The above results show that in up to 1000 hours of exposure, the UV stabilizers of the present invention significantly enhance the UV stability of the polycarbonate sheet.

EXAMPLE 6

Plaques of molded Lexan ® polycarbonate were made by extruding a blend of 1350 parts of air dried polycarbonate and 4.5 parts of UV stabilizer. The plaques were aged under an RS sun lamp as described in Example 5. The ΔYI of the slabs aged for 7 days are as follows:

TABLE II

| | ΔYI |
| --- | --- |
| 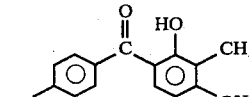 | 2.6 |
| 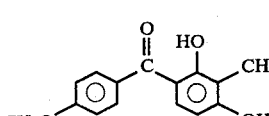 | 3.6 |
| 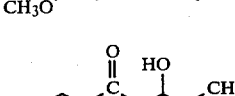 | 7.0 |
| 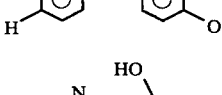 | 12.1 |

The above results show that the UV stabilizers of the present invention are superior to the hydroxyphenylbenzotriazoles of the prior art with respect to reducing polycarbonate degradation.

EXAMPLE 7

An extruded Lexan polycarbonate slab is dipped for 30 seconds into a solution of 1 part of 1,2-dichloropropane and 10 parts of m-xylene and 5% by weight of the UV stabilizer of Example 1. The sheet is dried at 70° C. for one hour. A similar slab is treated following the same procedure, except that hydroxyphenylbenzotriazole is substituted for the UV stabilizer of Example 1. It is found that the UV stabilizer of Example 1 is superior to hydroxyphenylbenzotriazole following the above yellowing index test.

Although the above examples are directed to only a few of the very many variables of the present invention, it should be understood that the present invention is directed to a much broader variety of UV stabilizers of formula (1), coating compositions containing such stabilizers in combination with organic resin as previously defined and composite structures treated with such coating composition.

What I claim as new and desire to secure by Letters Patent of the United States is:

1. A coating composition comprising
   (A) an organic resin selected from the class consisting of a melamine resin, an acrylic resin, and a silicon resin and
   (B) a stabilizing amount of a UV stabilizer selected from the class consisting of 2,4-dihydroxy-4'-methoxy-3-methylbenzophenone and 3-methyl-2,4,4'-trihydroxybenzophenone.

2. A coating composition in accordance with claim 1, where the melamine resin is a mixture of a melamine compound of the formula,

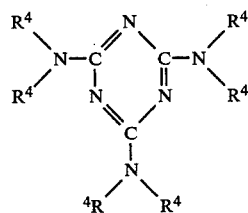

and a polyhydroxy organic compound, where $R^4$ is selected from the class of H, —$CH_2OH$, and —$CH_2O(CH_2)_xH$, where x is an integer of from 1 to 4.

3. A composite structure comprising
   (A) A thermoplastic organic polymer sheet and
   (B) A cured coating of organic resin having a stabilizing amount of a UV stabilizer selected from the class consisting of 2,4-dihydroxy-4'-methoxy-3-methylbenzophenone and 3-methyl-2,4,4'-trihydroxybenzophenone.

4. A shaped organic thermoplastic part comprising a thermoplastic organic resin and 0.1 to 1% by weight of a UV stabilizer selected from the class consisting of 2,4-dihydroxy-4'-methoxy-3-methylbenzophenone and 3-methyl-2,4,4'-trihydroxybenzophenone.

5. A thermoplastic organic polymeric sheet surface impregnated with a stabilizing amount of a UV stabilizer selected from the class consisting of 2,4-dihydroxy-4'-methoxy-3-methylbenzophenone and 3-methyl-2,4,4'-trihydroxybenzophenone.

* * * * *